(12) United States Patent
Bruckner et al.

(10) Patent No.: US 6,645,979 B2
(45) Date of Patent: Nov. 11, 2003

(54) (7-(3-CARBOXYPHENYL)-4-CHLOROISOQUINOLIN-1-YL)GUANIDINE

(75) Inventors: Anne Bruckner, County of Kent (GB); Michael Butters, County of Kent (GB); Paul Vincent Fish, County of Kent (GB); Michael Paul Fitzgerald, County of Kent (GB); Julie Ann Macrae, County of Kent (GB); Trevor Jack Newbury, County of Kent (GB); Richard Anthony Storey, County of Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/005,587

(22) Filed: Oct. 29, 2001

(65) Prior Publication Data

US 2002/0077336 A1 Jun. 20, 2002

Related U.S. Application Data

(60) Provisional application No. 60/253,435, filed on Nov. 28, 2000.

(30) Foreign Application Priority Data

Oct. 30, 2000 (GB) ................................ 0026490

(51) Int. Cl.⁷ ................................ A01N 43/42
(52) U.S. Cl. ...................... 514/310; 546/143
(58) Field of Search ........................ 514/310; 546/143

(56) References Cited

U.S. PATENT DOCUMENTS

6,248,738 B1 * 6/2001 Dickinson ............... 514/568.2

FOREIGN PATENT DOCUMENTS

| EP | 0629631 | 12/1994 |
| WO | 99/20608 | * 4/1999 |

* cited by examiner

Primary Examiner—D. Margaret Seaman
(74) Attorney, Agent, or Firm—Adrian G. Looney; Claude F. Purchase, Jr.

(57) ABSTRACT

The invention described herein relates to a process for the preparation of (7-(3-carboxyphenyl)-4-chloroisoquinolin-1-yl)guanidine (I), intermediates thereto and new forms and formulations thereof, including the zwitterion monohydrate of (I), suitable for pharmaceutical use.

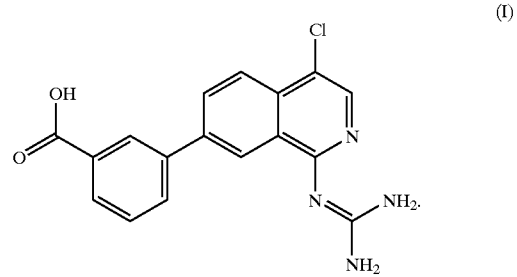

(I)

11 Claims, 5 Drawing Sheets

(7-(3-CARBOXYPHENYL)-4-CHLOROISOQUINOLIN-1-YL)GUANIDINE

The application claims the benefit of U.S. Provisional Patent Application No. 60/253,435, filed Nov. 28, 2000 and U.K. Patent Application No. 0026490.3, filed Oct. 30, 2000, both of which are hereby incorporated by reference in their entirety.

BACKGROUND OF THE INVENTION

This invention relates to a process for the preparation of (7-(3-carboxyphenyl)-4-chloroisoquinolin-1-yl)guanidine (I), intermediates thereto and new forms and formulations thereof suitable for pharmaceutical use.

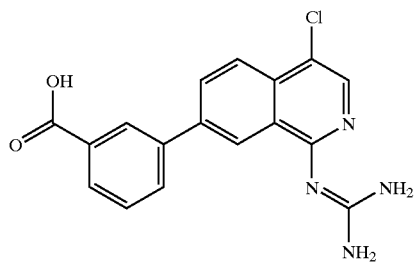

International Patent Application publication no. WO 99/20608, which is herein incorporated by reference in its entirety, discloses certain isoquinolinylguanidine compounds as antagonists of urinary-type plasminogen activator ("uPA", also known as urokinase, International Union of Biochemistry classification number EC.3.4.21.31), including the hydrochloride salt of (7-(3-carboxyphenyl)-4-chloroisoquinolin-1-yl)guanidine (I) (Example 55 therein). Compound (I) is a potent uPA antagonist and is thus likely to be useful in the treatment of conditions mediated by uPA. Such treatments are mentioned in WO 99/20608. For a number of such treatments, administration of an aqueous topical formulation which can be sterilised is desirable.

It is desirable, for the treatment of some of the conditions mediated by uPA, to formulate compound (I) as a suspension drug product. As such stability to autoclaving as the preferred method of sterilisation is important. Treatment of some of the conditions in certain ways requires stability in an aqueous environment. Also important is the shelf-life of the formulation, with a target stability of ca. 2 years at ambient temperature. The stability of the bulk form is also important as any changes in the form of the active substance may compromise the product's clinical and/or safety performance.

The hydrochloride salt of (I) has certain properties which make it particularly unsuitable for pharmaceutical formulation in a base suitable for topical administration, e.g. to a wound, such as poor physical stability at relevant pH (>4), poor crystallinity, etc. The scale-up of the process to make the hydrochloride salt of (I) disclosed in WO 99/20608 has disadvantages. In WO 99/20608, the hydrochloride salt of (I) is made from the corresponding nitrile by hydrolysis with hydrochloric acid. Acid-catalysed hydrolysis of the nitrile has been found to give rise to undesirable levels of certain side-reactions, such us under-hydrolysis of the nitrile moiety to give the corresponding carbamoyl compound, and over-hydrolysis at the guanidine moiety to give the corresponding amine. The route to the hydrochloride salt of (I) described in WO 99/20608 has a number of other disadvantages which make it undesirable for scale-up, such as handling and purification difficulties of certain intermediates. A number of alternative routes, salts and solvates were explored with a view to solving the above-mentioned problems.

SUMMARY OF THE INVENTION

The problems outlined above have been solved by the provision of a zwitterion monohydrate of (I), i.e. (IA) in the scheme below, and processes and intermediates thereto. Other aspects of the invention include formulations of the zwitterion monohydrate (IA), and uses thereof.

The invention further provides methods for the production of substances of the invention, which are described below and in the Examples. The skilled person will appreciate that the substances of the invention could be made by methods other than those herein described, by adaptation of the methods herein described in the sections below and/or adaptation thereof, and of methods known in the art.

It will be appreciated that tautomers and geometric isomers of the compounds disclosed herein are included within the scope of this invention. For example the compound referred to as the "zwitterion monohydrate" (IA) is herein also referred to (e.g. in the scheme) as the guanidine/acid hydrate, i.e. having N=C(NH$_2$)$_2$/CO$_2$H groups. In aqueous solution at neutral or near-neutral pH, it is believed to exist mainly in the zwitterionic form, i.e. with the guanidinium moiety and a carboxylate moiety. The two tautomeric forms of the guanidine moiety are N=C(NH$_2$)$_2$ and NHC(=NH)(NH$_2$).

DETAILED DESCRIPTION OF THE INVENTION

Figure 1:
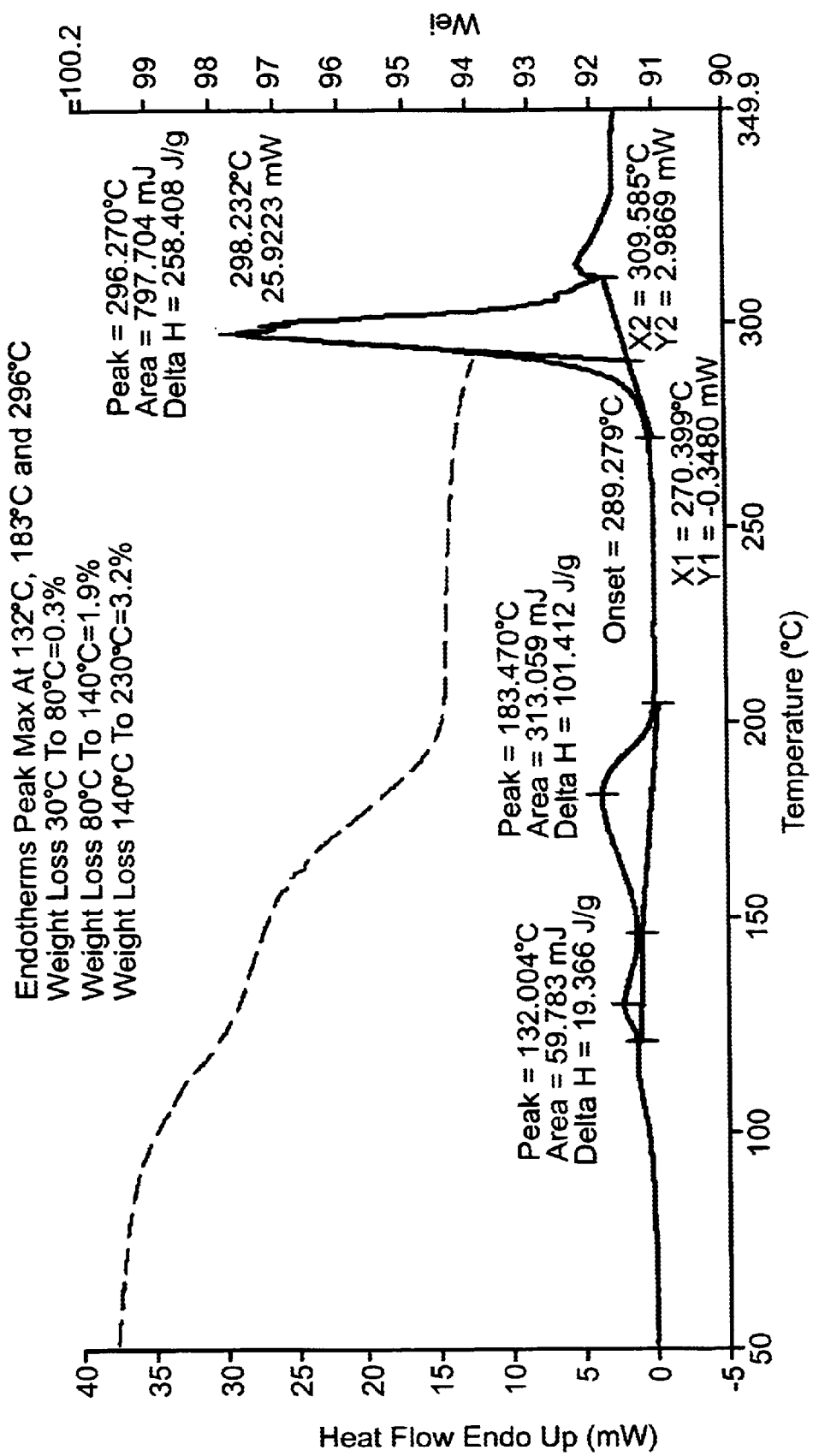
FIG. 1. is a DSC/TGA analysis plot for the monohydrate (IA) prepared in Example 9.

The zwitterion monohydrate (IA) can be prepared according to the process as outlined in the Scheme below. Examples of reagents which can effect the transformations are mentioned in A–J below.

The skilled person will appreciate that the substances described herein may also be made by methods other than those specifically described herein, by adaptation of the methods herein described in the sections below and/or adaptation thereof, for example by methods known in the art. Suitable guides to synthesis, functional group transformations, use of protecting groups, etc. are, for example, "Comprehensive Organic Transformations" by R C Larock, VCH Publishers Inc. (1989), "Advanced Organic Chemistry" by J March, Wiley Interscience (1985), "Designing Organic Synthesis" by S Warren, Wiley Interscience (1978), "Organic Synthesis—The Disconnection Approach" by S Warren, Wiley Interscience (1982), "Guidebook to Organic Synthesis" by R K Mackie and D M Smith, Longman (1982), "Protective Groups in Organic Synthesis" by T W Greene and P G M Wuts, John Wiley and Sons Inc. (1999), and P J Kocienski, in "Protecting Groups", Georg Thieme Verlag (1994), and any updated versions of said standard works.

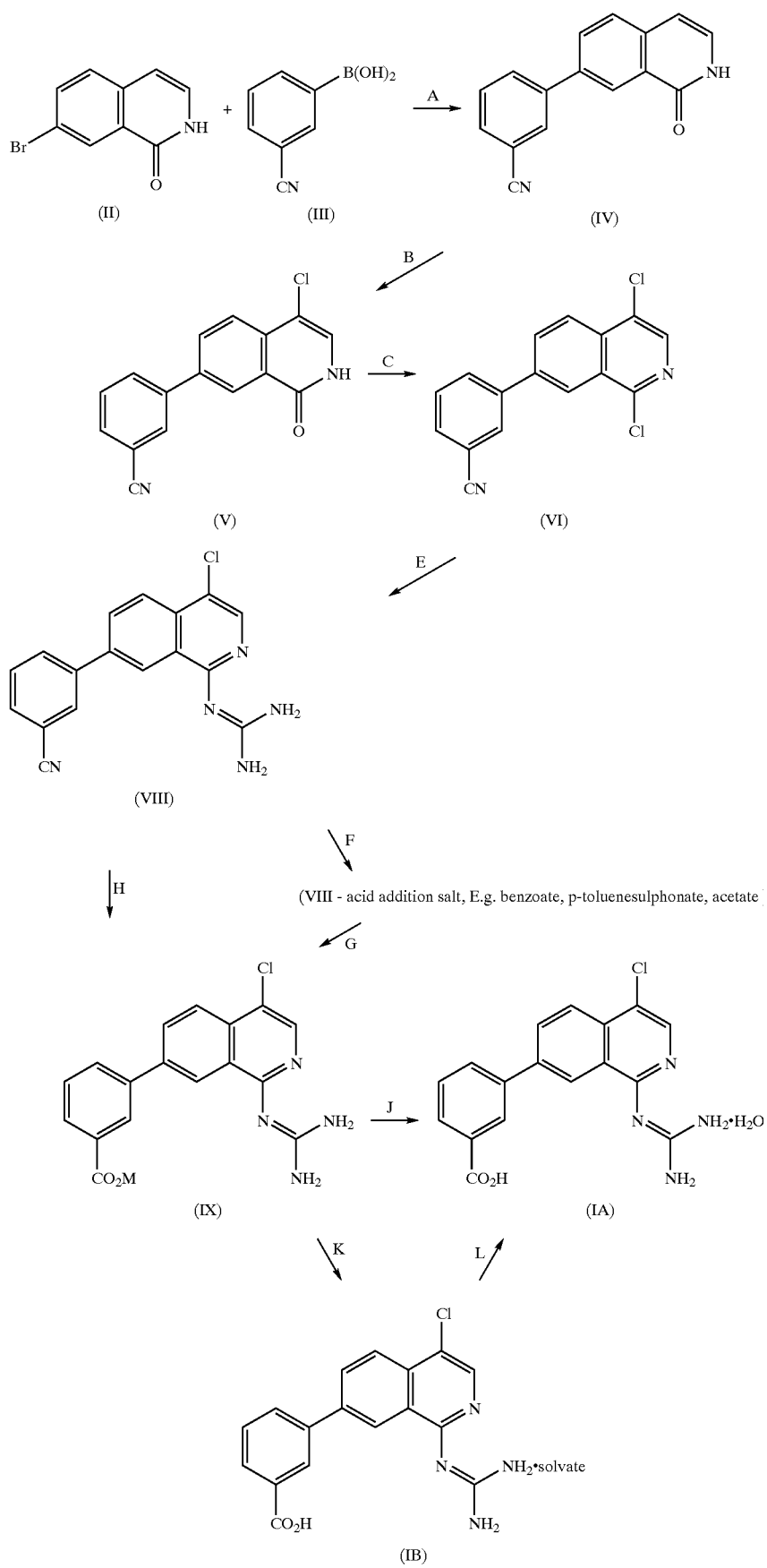

A. aq. NaOH, palladium acetate, MeOH; B. source of "Cl+", e.g. N-chlorosuccinimide; C.chlorinating agent such as POCl₃; E. Guanidine source; F. Acid such as acetic, benzoate, p-toluenesulphonic, or (R)-camphorsulphonic acid; G. aq. MOH, e.g. aq.LiOH; H aq. MOH, e.g. aq.LiOH; J. aq. weak acid, e.g. aq.NH₄Cl; K. weak acid/solvent; L. water The zwitterion monohydrate (IA) can be made by reaction of a metal carboxylate salt (IX) wherein M is Na, K, or Li, with an acid, preferably a weak acid such as NH₄Cl, in an aqueous environment, suitably in an inert solvent such as dimethylsulphoxide (DMSO), N-methylpyrrolidone (NMP) or N,N-dimethylformamide (DMF).

Preferably the metal salt (IX) is dissolved in the solvent, and a weak acid is slowly added in solution at an elevated temperature such as about 100° C. Preferably the reaction is carried out under an inert atmosphere such as under nitrogen. Typically, at the end of the reaction and after the reaction mixture has cooled, the zwitterion monohydrate (IA) precipitates and can be collected by filtration or other suitable means.

In some cases the reaction of (IX) with the acid in a solvent, e.g. where there is no water, or only a small amount thereof, may result in the formation of a zwitterion solvate (IB) where "solvate" is not a hydrate. An example of this is the zwitterion DMSO solvate.

Solvates (IB) can be converted into the hydrate (IA) by reaction with water, as exemplified below.

Solvates (IB), if desired, may alternatively be made by treating hydrate (IA) with an appropriate non-aqueous solvent, and driving off the water from the hydrate.

The metal carboxylate salt (IX) can be made by reaction of nitrile (VIII), or an acid salt thereof such as the acetate, benzoate or p-toluenesulphonate, with a base such as aqueous MOH where M is a metal, preferably a group IA metal such as Na, K or Li. Suitably the reaction is carried out in a solvent such as in an alcoholic solvent, e.g. "industrial methylated spirits" (IMS). The reaction is typically carried out at an elevated temperature, and a suitable temperature is the reflux temperature of the solvent. Preferably the reaction is carried out under an inert atmosphere such as under nitrogen.

It has been found that in some circumstances the sodium and potassium carboxylates (IX, M=Na or K), when made by hydrolysis of nitrile (VIII), or acid salt thereof, with aqueous NaOH or KOH respectively, form as gels. The lithium salt (IX, M=Li) is preferred as it forms a solid which is easier to handle, filter and hence purify.

An acid salt of (VIII), such as the acetate, benzoate or p-toluenesulphonate salt, may be preferred as an intermediate, as this may offer a material which may be easier to handle/purify than the free base. The acidification of (VIII) is straightforward (e.g. with acetic or benzoic or p-toluenesulphonic acid) and offers a further optional purification method for (VIII).

The benzoate salt of (VIII) is preferred, especially in combination with the use of guanidine carbonate in the previous reaction. One of the impurities produced using the guanidine carbonate reaction was removed using the benzoate purification, whereas this did not happen using the acetate method. It was found that filtration of the benzoate gave superior purity and filtration results compared to the acetate.

The preparation of compound (VIII) is described in International Patent Application publication no. WO 99/20608 (Example 41 therein). The guanylation is suitably carried out using a guanidine salt and a suitable base, or alternatively using guanidine carbonate. Use of guanidine carbonate offers the advantages of being a quicker and more robust reaction, and has a superior impurity profile, especially when used in conjunction with the use of the benzoate salt of (VIII) (see above).

The preparation of compound (VI), from 7-bromo-1,4-dichloroisoquinoline and 3-cyanophenylboronic acid, is described in International Patent Application publication no. WO 99/20608 (Preparation 37 therein).

A further method of preparing compound (VI) is via reaction of the isoquinolone (V) with a chlorinating agent such as PCl₃, POCl₃ or PCl₅, suitably as a "melt" or in an inert solvent such as acetonitrile (MeCN), suitably at an elevated temperature such as the reflux temperature of MeCN.

Compound (V) is available via chlorination of the isoquinolone (IV) with an agent that is equivalent to a "Cl+" synthon, such as N-chlorosuccinimide or PCl₅, suitably in an inert solvent such as N,N-dimethylacetamide (DMA), and suitably at an elevated temperature such as the reflux temperature of DMA.

Compound (IV) can be made by reaction of 7-bromoisoquinoline (II) (WO 99/20608, Preparation 3 (iii)) with 3-cyanophenylboronic acid (III) (WO 94/11372) in a Suzuki-type reaction. Alternatively a Stille coupling reaction could be used for this step.

Solvates of the zwitterion of (I) above can also be made by treatment of an acid salt of (I), such as the hydrochloride salt mentioned in WO 99/20608 (Example 55 therein), with a suitable base such as a hydroxide of a Group I metal, such as sodium hydroxide, lithium hydroxide, etc. in a suitable solvent such as methanol (e.g. as IMS). An alternative preparation of the hydrate of this type is mentioned in the Examples below.

For human use, the substance of formula (IA) can be administered alone, but will generally be administered in admixture with a pharmaceutically acceptable adjuvant, diluent or carrier selected with regard to the intended route of administration and standard pharmaceutical practice. For example, it can be administered orally, including sublingually, in the form of tablets containing such excipients as starch or lactose, or in capsules or ovules either alone or in admixture with excipients, or in the form of elixirs, solutions or suspensions containing flavouring or colouring agents, or as an implant. It can be injected parenterally, for example, intravenously, intramuscularly or subcutaneously. For parenteral administration, it is best used in the form of a sterile aqueous solution or suspension which may contain other substances, for example, enough salt or glucose to make the solution isotonic with blood. It can be administered topically, in the form of sterile creams, gels, suspensions, lotions, ointments, dusting powders, sprays, foams, films, sponges, fibres, drug-incorporated dressings or via a skin patch. For example it can be incorporated into a cream consisting of an aqueous or oily emulsion of polyethylene glycols or liquid paraffin, or it can be incorporated into an ointment consisting of a white wax soft paraffin base, or as hydrogel with cellulose or polyacrylate derivatives or other viscosity modifiers, or as a dry powder or liquid spray or aerosol with butane/propane, HFA or CFC propellants, or as a drug-incorporated dressing either as a tulle dressing, with white soft paraffin or polyethylene glycols impregnated gauze dressings or with hydrogel, hydrocolloid, alginate or film dressings. It could also be administered intraocularly as an eye drop with appropriate buffers, viscosity modifiers (e.g. cellulose derivatives), preservatives (e.g. benzalkonium chloride (BZK)) and agents to adjust tenicity (e.g. sodium chloride).

As mentioned earlier, for some treatment and administration methods, a suspension drug product may be desired. Typically a suspension drug product will include one or more polymer (e.g. a water swellable or water soluble polymer) that can gel, thicken, disperse or dissolve in aqueous or partially aqueous systems/systems that contain water and other pharmaceutically acceptabe excipients, e.g. in a gel (including hydrogel) system. Such polymers are well known in the art and can include starch and starch derivatives, galactomannan and galactomannan derivatives, chitosan and chitosan derivatives, glycoproteins, proteoglycans, glucosaminoglycans, vinyl pyrrolidone/vinyl acetate co-polymers, high molecular weight polypropylene glycols, acemannan, chondroitin sulphate, dextrin, dextran.

Further suitable gelling agents can be selected from natural polysaccharides, semisynthetic polysaccharides, synthetic polymers, colloidally dispersed solids, clays, etc., suitable examples of which are mentioned below. Again, these can be used on their own or in combinations.

Examples of natural polysaccharides: acacia (gum arabic); acemannan; agar; alginic acid and its salts; kappa-/iota carrageenan; chitosan and chitosan derivatives; chondroitin sulphate; dextrin; dextran; galactomannan and galactomannan derivatives; gellan gum; glucosaminoglycans; glycyrrhizin; guar gum; hyaluronic acid/sodium hyaluronate; hyaluronic acid esters; karaya gum; locust bean gum (carob gum); pectin; starch and starch derivatives; tragacanth gum; xanthan gum.

Examples of semisynthetic polysaccharides: carboxymethyl cellulose (CMC) and CMC sodium; hydroxyethyl cellulose (HEC); hydroxyethylmethyl cellulose (HEMC); hydroxypropyl cellulose (HPC); hydroxypropylmethyl cellulose (HPMC); methyl cellulose (MC); propylene glycol alginate.

Examples of synthetic polymers: Carbomer (different Carbopol® grades); poloxamer (Pluronic® grades); polyacrylamide; glyceryl polyacrylate; polyethylene glycols (PEGS); polyvinylpyrrolidone (PVP); polyvinyl alcohol (PVA); vinyl pyrrolidone/vinylacetate co-polymers; polypropylene glycols (high MWts).

Examples of colloidally dispersed solids: microcrystalline silica; microcrystalline cellulose; microcrystalline cellulose; CMC sodium (Avicel RC-591); clays (e.g. Bentonite).

Examples of proteins: collagen; gelatin; glycoproteins; proteoglycans.

Other excipients may also be useful in the formulation, and can be used in accordance with standard pharmaceutical formulation practice, such as surfactants, tonicity adjusting agents, buffers, etc.

The following formulation texts are herein incorporated by reference with regard to the polymers and other excipients:
Pharmaceutical Dosage Forms: Disperse Systems
(Vol. 2—Chapter 10; Gels; J. L. Zatz, G. P. Kushla)
Editors: H. A. Lieberman, M. M. Rieger, G. S. Banker
Publisher: Marcel Dekker, Inc; 1998
Martindale. The Extra Pharmacopoeia; 31st Edition
"Stabilising and Suspending Agents"
Editor: J. E. F. Reynolds
Publisher: The Pharmaceutical Press; 1996
Encyclopedia of Pharmaceutical Technology
(Vol. 6—"Gels and Jellies"; Cathy M. Klech)
Editors: J. Swarbrick, J. C. Boylan
Publisher: Marcel Dekker, Inc; 1992
Handbook of Water-Soluble Gums and Resins
Editor: R. L. Davidson
Publisher: McGraw-Hill Book Company; 1980
Martindale. The Extra Pharmacopoeia; 31 st Edition
Editor: J. E. F. Reynolds
Publisher: The Pharmaceutical Press; 1996
Remington: The Science and Practice of Pharmacy; 20th Edition
Editor: Alfonso R. Gennaro
Publisher: Mack Publishing Co; 2000
Handbook of Pharmaceutical Excipients, 3rd Edition
Editor: Arthur H. Kibbe
Publisher: American Pharmaceutical Association and The Pharmaceutical Press;
2000

For oral and parenteral administration to human patients, the daily dosage level of (IA) will be from 0.001 to 20, preferably from 0.01 to 20, more preferably from 0.1 to 10, and most preferably from 0.5 to 5 mg/kg (in single or divided doses). Thus tablets or capsules of the substance will contain from 0.1 to 500, preferably from 50 to 200, mg of active compound for administration singly or two or more at a time as appropriate.

The physician in any event will determine the actual dosage which will be most suitable for a an individual patient and it will vary with the age, weight and response of the particular patient. The above dosages are exemplary of the average case; there can of course be individual instances where higher or lower dosage ranges are merited, and such are within the scope of this invention.

Another aspect of the invention is a pharmaceutical composition comprising the monohydrate (IA), including the zwitterion and tautomers thereof, and a pharmaceutically-acceptable adjuvant, carrier or diluent.

Another aspect of the invention is the monohydrate (IA), including the zwitterion and tautomers thereof, for use as a medicament.

Another aspect of the invention is the monohydrate (IA), including the zwitterion and tautomers thereof, for use as a medicament useful for treating a uPA-mediated condition.

Another aspect of the invention is the use of the monohydrate (IA), including the zwitterion and tautomers thereof, for the manufacture of a medicament for the treatment of a condition or process mediated by uPA, such as chronic dermal ulcer, angiogenesis (neo-vascularization), bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

Another aspect of the invention is a method of treatment of a condition or process mediated by uPA, such as chronic dermal ulcer, angiogenesis (neo-vascularization), bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis, comprising administering a therapeutic amount of the monohydrate (IA), including the zwitterion and tautomers thereof.

Preferably the condition to be treated is a chronic dermal ulcer such as a decubitus ulcer (pressure sore), venous ulcer or diabetic foot ulcer.

Another aspect of the invention is a pack comprising:

the monohydrate (IA), including the zwitterion and tautomers thereof, optionally in a pharmaceutical composition comprising a pharmaceutically-acceptable adjuvant, carrier or diluent;

directions instructing the user on the treatment of a uPA-mediated condition; and packaging.

It is to be appreciated that reference to treatment includes prophylaxis as well as the alleviation of established symptoms of uPA-mediated conditions.

EXAMPLES

Melting points were determined using open glass capillary tubes and a Gallenkamp melting point apparatus and are uncorrected. Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. Infra red (IR) spectra were measured using a Nicolet Magna 550 Fourier transform infra-red spectrometer. Powder X-Ray Diffraction data was obtained using a Siemens D5000 Powder X-Ray diffractometer. Differential Scanning Calorimetry data was obtained using a Perkin Elmer 7/TA Instruments 2910. Thermogravimetric Analysis data was obtained using a Perkin Elmer 7/TA Instruments Hi-Res 2950. Light Microscopy data was obtained using a Nikon Labophot. Hot Stage Microscopy data was obtained using a Linkam TMS 92. Karl Fischer Titrimetry data was obtained using a Mitsubishi CA-06.

Nomenclature has been allocated using a program available from IUPAC. Standard abbreviations are used throughout, e.g. "Me" is methyl, "Et" is ethyl, "Pr" is propyl, etc.;

"DMA" is dimethylacetamide; "MeCN" is acetonitrile; "DME" is dimethoxyethane; "NMP" is N-methylpyrrolidone; "IMS" is industrial methylated spirits; "DMSO" is dimethylsulphoxide, etc.

Example 1

7-(3-Cyanophenyl)isoquinolinone (IV)

A solution of sodium hydroxide (214 g, 5.35 mol) in water (10 L) was added to a stirred suspension of 3-cyanophenylboronic acid (24% water content, 1.13 kg, 5.8 mol) and 7-bromoisoquinolinone (1.0 kg, 4.46 mol) in methanol (10 L) and the mixture stirred for 1 hour. Palladium acetate (10 g, 44.5 mmol) was added and the mixture was heated at reflux under $N_2$ for 5 hours and then cooled to room temperature and stirred overnight. The light grey solid was collected by filtration. The damp solid was reslurried in water (10 L) and heated to 80° C. for 30 minutes. The mixture was then cooled to room temperature and the solid collected by filtration, washed with water (2 L) then methanol (2 L) and dried in vacuo at 50° C. to give 7-(3-cyanophenyl)isoquinolinone (1.09 kg, 4.43 mol, 99%) as a light grey solid.

Mp>300° C.

$^1$H (TFAD, 300 MHz) δ 8.78 (1H, s), 8.28 (1H, d), 8.09 (3H, m), 7.84 (1H, d), 7.74 (2H, m), 7.51 (1H, d) ppm.

Example 2

4-Chloro-7-(3-cyanophenyl)isoquinolinone (V)

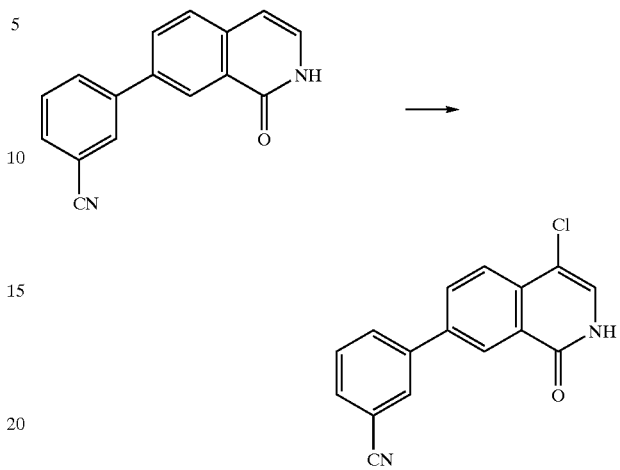

A solution of N-chlorosuccinimide (307 g, 2.3 mol) in DMA (1.2 L) was added to a stirred suspension of 7-(3-cyanophenyl)isoquinolinone (0.54 kg, 2.2 mol) in boiling DMA (3.9 L) over a period of 1 hour under $N_2$. The mixture was heated at reflux overnight and cooled to room temperature. The solid was collected by filtration, washed with MeCN (1.0 L) and dried in vacuo at 50° C. to give 4-chloro-7-(3-cyanophenyl)isoquinolinone (0.5 kg, 1.78 mol, 81%) as an off white solid.

Mp>300° C.

$^1$H (DMSO-$d_6$ 300 MHz) δ 11.66 (1H, s), 8.53, (1H, s), 8.25 (1H, dd), 8.13 (1H, dd), 7.90 (1H, d), 7.81 (1H, d), 7.71 (1H, t), 7.53 (1H, s) ppm

Example 3

1,4-Dichloro-7-(3-cyanophenyl)isoquinoline (VI)

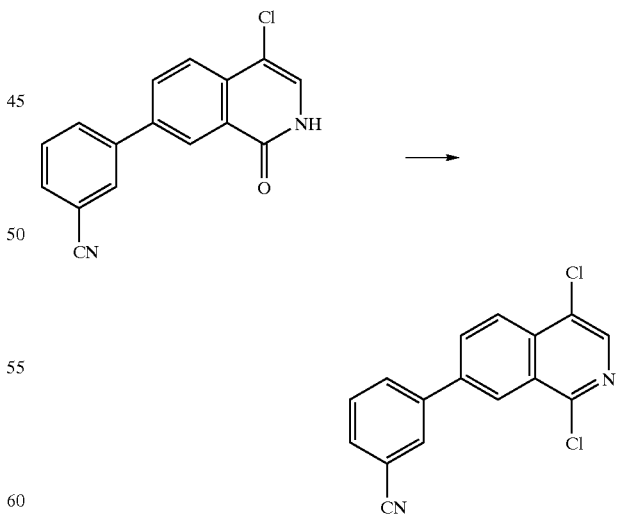

(i) A solution of $POCl_3$ (8.36 kg, 54.5 mol) in MeCN (11.5 L) was added to a suspension of 4-chloro-7-(3-cyanophenyl)isoquinolinone (7.65 kg, 27.3 mol) in boiling MeCN (65 L) under $N_2$ over 1 hour. The mixture was heated at reflux for 11 hours and then cooled to room temperature. The mixture was slowly quenched with 1N aqueous HCl (38.3 L) and the resultant slurry stirred for 1 hour. The solid was collected by filtration, washed with MeCN (7.6 L) and dried in vacuo at 50° C. to give 1,4-dichloro-7-(3-cyanophenyl)isoquinoline (7.20 kg, 24.1 mol, 88%) as a creamy coloured solid.

Mp>300° C.

$^1$H (DMSO-$d_6$ 300 MHz) δ 8.59 (1H, d), 8.53 (1H, s), 8.45 (1H, m), 8.34 (1H, d), 8.23 (1H, d), 7.95 (1H, d), 7.76 (1H, t) ppm.

alternative preparation:

(ii) A solution of POCl$_3$ (0.545 kg, 3.56 mol) in MeCN (0.76 L) was added to a suspension of 4-chloro-7-(3-cyanophenyl)isoquinolinone (0.50 kg, 1.78 mol) in boiling MeCN (4.25 L) under N$_2$ over 1 hour. The mixture was heated at reflux overnight and then cooled to room temperature. The solid was collected by filtration, washed with MeCN (0.5 L) and dried in vacuo at 70° C. to give 1,4-dichloro-7-(3-cyanophenyl)isoquinoline (0.54 kg) as a creamy coloured solid which could be used without further drying or purification. The filtrate was slowly quenched with HCl (1N; 2.6 mL) which gave a second crop of 60 g of material which was filtered and washed with MeCN (0.5 L), which again could be used without further drying or purification.

Example 4

(4-Chloro-7-(3-cyanophenyl)isoquinolin-1-yl) guanidine (VIII)

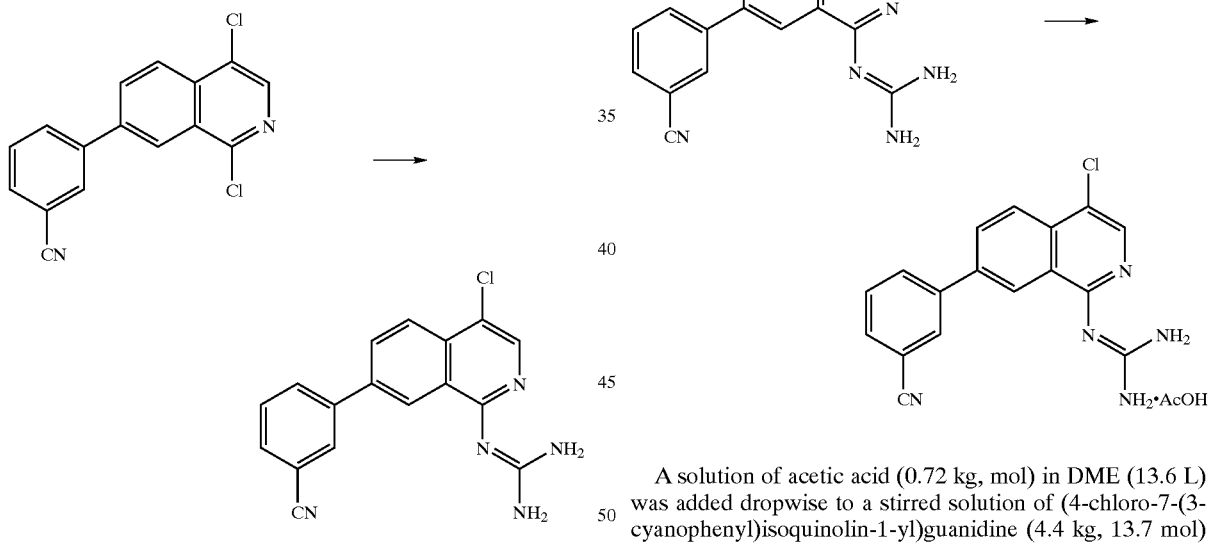

(i) A stirred suspension of guanidine hydrochloride (3.8 kg, 39.8 mol) and KO$^t$Bu (4.28 kg, 38.1 mol) in DME (17.6 L) was heated to reflux under N$_2$ for 1 hour. The gum containing solution was cooled to room temperature, diluted with NMP (8.8 L) and 1,4-dichloro-7-(3-cyanophenyl)isoquinoline (4.4 kg, 14.7 mol) was added as a solid. The mixture was heated at reflux overnight, cooled to room temperature, filtered through a pad of celite and the pad washed with DME (4.4 L). Water (35.2 L) was added to the filtrate. The resultant slurry was stirred for 2 hour and the solid collected by filtration. The solid was washed with water (4.4 L) and dried in vacuo at 50° C. to give (4-chloro-7-(3-cyanophenyl)isoquinolin-1-yl)guanidine (4.55 kg, 14.1 mol, 96%) as a green solid.

Mp>300° C.

$^1$H (DMSO-$d_6$ 300 MHz) δ 8.97 (1H, d), 8.19 (1H, t) 8.13 (1H, dd), 8.08 (1H, d), 8.00 (1H, s), 7.95 (1H, d), 7.86 (1H, br.d), 7.72 (1H, t) ppm.

alternative preparation:

(ii) A stirred suspension of guanidine carbonate (720 g, 4.0 mol) in NMP (5 L) was heated to 130° C. under N$_2$ for 1 hour. The suspension was cooled to room temperature and 1,4-dichloro-7-(3-cyanophenyl)isoquinoline (1.0 kg, 3.3 mmol) was added as a solid. The mixture was heated at 130° C. for 4 hours, cooled to room temperature, filtered through a pad of clarcel. Water (6.7 L) was added to the filtrate. The resultant slurry was cooled to 5° C., stirred for 1 hour and the solid collected by filtration. The solid was washed with a mixture of NMP:water (1:1, 4 L) and water (4 L) and dried in vacuo at 50° C. to give (4-chloro-7-(3-cyanophenyl) isoquinolin-1-yl)guanidine (900 g, 2.8 mol, 85%) as a green solid.

alternative preparation (ii)(a) as, (ii) but the guanidine carbonate and compound (VI) are mixed before heating to 130° C.

Example 5

4-Chloro-7-(3-cyanophenyl)isoquinolin-1-yl) guanidinium acetate (VIII—acetate salt)

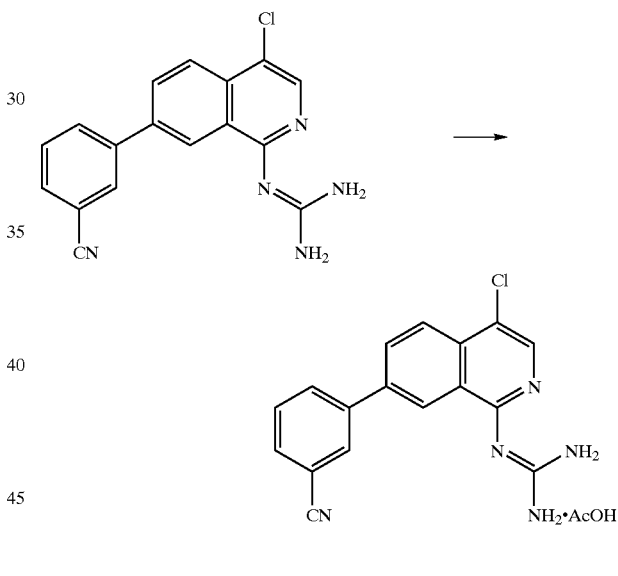

A solution of acetic acid (0.72 kg, mol) in DME (13.6 L) was added dropwise to a stirred solution of (4-chloro-7-(3-cyanophenyl)isoquinolin-1-yl)guanidine (4.4 kg, 13.7 mol) in NMP (14 kg) at 100° C. After addition the thick slurry was allowed to cool and was stirred overnight at room temperature. The solid was collected by filtration, washed with DME (4.9 L) and dried overnight in vacuo at 50° C. to give (4-chloro-7-(3-cyanophenyl)isoquinolin-1-yl)guanidinium acetate (6 kg, 143%) as an NMP wet off white solid.

The wet solid was reslurried in acetone (41.7 L) and stirred at reflux for 1 hour. The slurry was cooled to room temperature, filtered and the cake washed with acetone (4.1 L) and dried in vacuo at 50° C. to give (4-chloro-7-(3-cyanophenyl)isoquinolin-1-yl)guanidinium acetate (3.35 kg, 8.78 mol, 64%)

Mp>300° C.

$^1$H (DMSO-$d_6$ 300 MHz) δ 8.98 (1H, s), 8.20 (1H, d) 8.13 (1H, dd), 8.10 (1H, d), 8.0 (1H, s), 7.96 (1H, d), 7.86 (1H, d), 7.72 (1H, t), 7.23 (5H, br.s), 2.48 (3H, br.s) ppm.

Other salts of (VIII) which have been made in a similar way are the benzoate, fumarate, salicylate, maleate, L-tartrate and succinate. These all formed solutions in dimethylacetamide and then crystallised overnight. Use of the benzoate salt results in a good quality of material being obtained.

Example 6

4-Chloro-7-(3-cyanophenyl)isoquinolin-1-yl) guanidinium benzoate (VIII—benzoate salt)

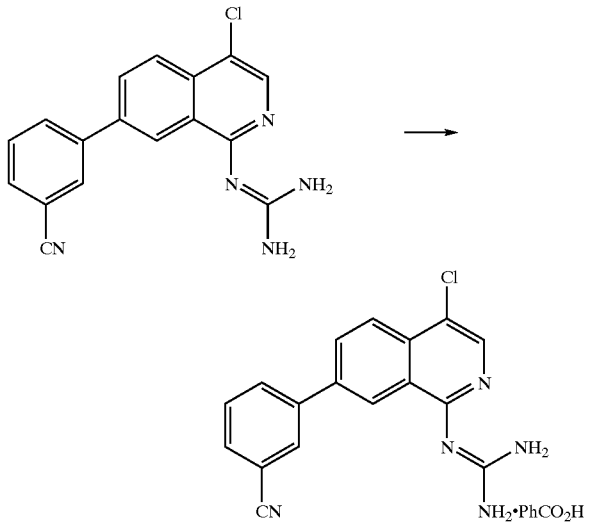

A slurry of benzoic acid (3.95 kg, 32.33 mol) and (4-chloro-7-(3-cyanophenyl)isoquinolin-1-yl)guanidine (10.2 kg, 31.69 mol) in DMA (61.2 L) was heated at 60° C. until dissolution was complete. The solution was slowly cooled to 40° C., seeded, granulated at 40° C. and then at ambient temperature. The thick slurry was cooled to 0° C., granulated, and the solid was collected by filtration, washed with DMA (5.1 L) and MeCN (10.2 L) and dried overnight in vacuo at 55° C to give (4-chloro-7-(3-cyanophenyl) isoquinolin-1-yl)guanidinium benzoate (9.85 kg, 22.19 mol, 70%) as an off white solid.

Mp>300° C.

$^1$H (DMSO-d$_6$, 400 MHz) δ 9.00 (1H, s), 8.21 (1H, s) 8.17 (1H, dd), 8.11 (1H, d), 8.04 (1H, s), 7.99 (1H, d), 7.92 (2H, d), 7.86 (1H, d), 7.68 (1H, t), 7.58 (1H, t), 7.46 (2H, t) ppm.

Example 7

(4-Chloro-7-(3-lithiumcarboxyphenyl)isoquinolin-1-yl)guanidine (IX) from (VIII—acetate salt)

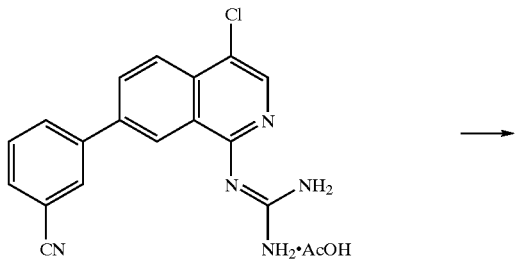

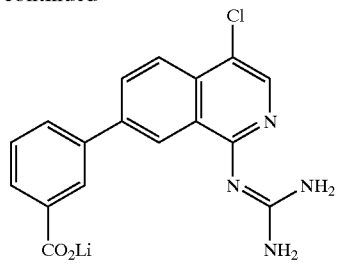

A solution of LiOH.H$_2$O (1.82 kg, 43.4 mol) in water (17.2 L) was added to a stirred suspension of (4-chloro-7-(3-cyanophenyl)isoquinolin-1-yl)guanidinium acetate (1.67 kg, 4.39 mol) in boiling IMS (27.1 kg) under N$_2$. The mixture was heated at reflux overnight and cooled to room temperature. The solid was collected by filtration and subsequently washed with IMS/water (2:1; 2.9 kg), then water (3.3 L) and finally IMS (3.3 L). The solid was dried in vacuo at 50° C. to give (4-chloro 7-(3-lithiumcarboxyphenyl)-isoquinolin-1-yl)guanidine (1.0 kg, 2.89 mol, 66%) as pale yellow solid.

Mp>300° C.

$^1$H (DMSO-d$_6$, 300 MHz) δ 8.96 (1H, d), 8.29 (1H, s) 8.05 (1H, dd), 7.95 (3H, m), 7.67 (1H, d), 7.51 (5H, br.s) 7.43 (1H, t) ppm.

Example 8

(4-Chloro-7-(3-lithiumcarboxyphenyl)isoquinolin-1-yl)guanidine (IX) from (VIII—benzoate salt)

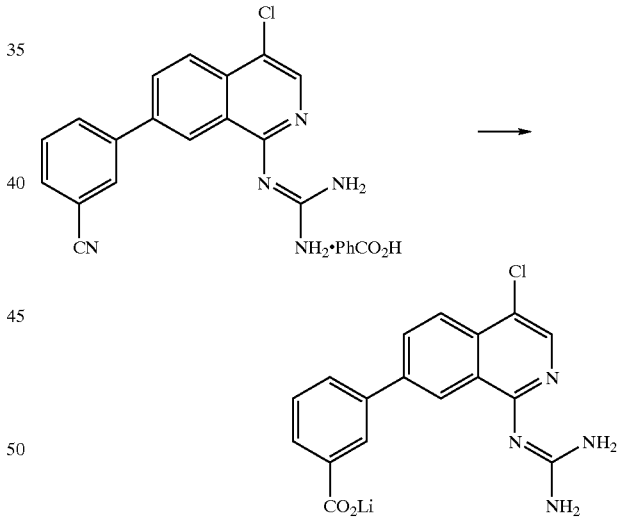

A solution of LiOH.H$_2$O (9.32 kg, 221.9 mol) in water (98.5 L) was added to a stirred suspension of (4-chloro-7-(3-cyanophenyl)isoquinolin-1-yl)guanidinium benzoate (9.85 kg, 22.19 mol) in boiling IMS (197 L kg) under N$_2$. The mixture was heated at reflux overnight and cooled to room temperature. The solid was collected by filtration and subsequently washed with IMS/water (2:1; 13L), then water (13 L) and finally IMS (13 L). The solid was dried in vacuo at 50° C. to give (4-chloro 7-(3-lithiumcarboxyphenyl)-isoquinolin-1-yl)guanidine (6.35 kg, 18.33 mol, 82.6%) as pale yellow solid.

Characterising data obtained were identical to that obtained from acetate salt hydrolysis.

Example 9

(4-Chloro-7-(3-carboxyphenyl)isoquinolin-1-yl)guanidine monohydrate (IA)

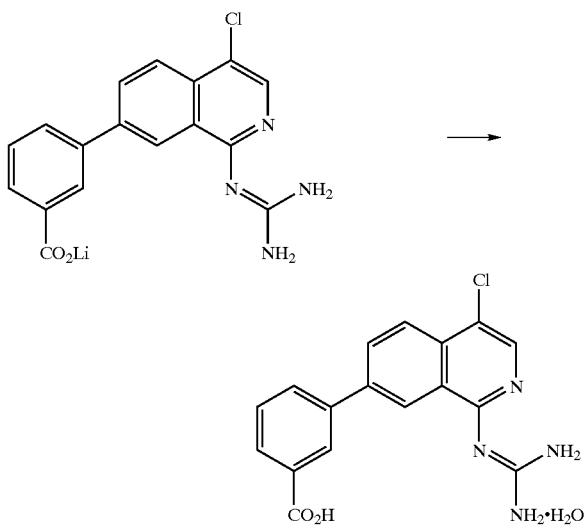

Method A.

(i) A solution of ammonium chloride (258 g, 4.82 mol) in water (30.4 L) was added slowly to a stirred 100° C. speck free solution of (4-chloro 7-(3-lithiumcarboxyphenyl)-isoquinolin-1-yl)guaninide (1.52 kg, 4.39 mol) in DMSO (30.4 L) under $N_2$. The mixture was heated for a further hour and then cooled to room temperature. The solid was collected by filtration and washed with speck free water (9 L). The damp cake was then reslurried in speck free water (30.4 L) for 30 minutes at room temperature, and then the solid collected by filtration. The solid was washed with speck free water (9 L), then speck free acetone (3 L) and then dried in vacuo at 40° C. to give (4-chloro 7-(3-carboxyphenyl)-isoquinolin-1-yl)guanidine monohydrate (1.26 kg, 3.52 mol, 80%) as an off-white solid.

Mp>300° C.

$^1$H (DMSO-$d_6$, 300 MHz) δ 8.96 (1H, s), 8.27 (1H, s) 8.11 (1H, d), 7.98 (4H, m), 7.63 (1H, t), 7.3 (3H, br.s) ppm.

Found C:56.53%, H: 4.17%, N:15.41%. Calculated for $C_{17}H_{13}ClN_4O_2.H_2O$: 56.91%, H:4.21%, N:15.62% alternative preparation:

(ii) Clarcel (1.1 kg) and water (12.7 L) were added to a solution of (4-chloro 7-(3-lithiumcarboxyphenyl)-isoquinolin-1-yl)guanidine (1.1 kg, 3.08 mol) in DMSO (22 L) under $N_2$. The mixture was stirred for 1 hour and then filtered. The filtrate was heated to 100° C. and a speck free solution of ammonium chloride (182 g, 3.4 mol) in water (11 L) was added slowly to it. The mixture was heated for a further hour and then cooled to room temperature. The solid was collected by filtration and washed with speck free water (2.2 L). The damp cake was then reslurried in speck free water (22 L) for 1 hour at room temperature, and then the solid collected by filtration. The solid was washed with water (4.4L), then acetone (2.2 L) and then dried in vacuo at 50° C. to give (4-chloro 7-(3-carboxyphenyl)-isoquinolin-1-yl)guanidine (760 g, 2.12 mol, 69%) as a pale yellow solid.

Method B.

Alternative preparation of (IA)

The hydrochloride salt of (I) (WO 99/20608, Example 55) (12.3 mg, 14.5 mg and 15.6 mg respectively) was dissolved in methanol (10 ml each). Sodium hydroxide (0.001 M in methanol, (32 μl, 38 μl and 41 μl respectively) was added and the mixtures became turbid. The solvents were removed (centrifuge evaporator) and the cream-coloured solid residues were washed in water (3.0 ml each). The solids were dried (centrifuge evaporator) and the three samples were combined, intimately mixed, washed with water (5 ml) and dried (centrifuge evaporator, then high vacuum) to give the zwitterion monohydrate (32.7 mg).

NMR and elemental analysis were fully consistent with the zwitterion monohydrate (IA).

Figure 2:
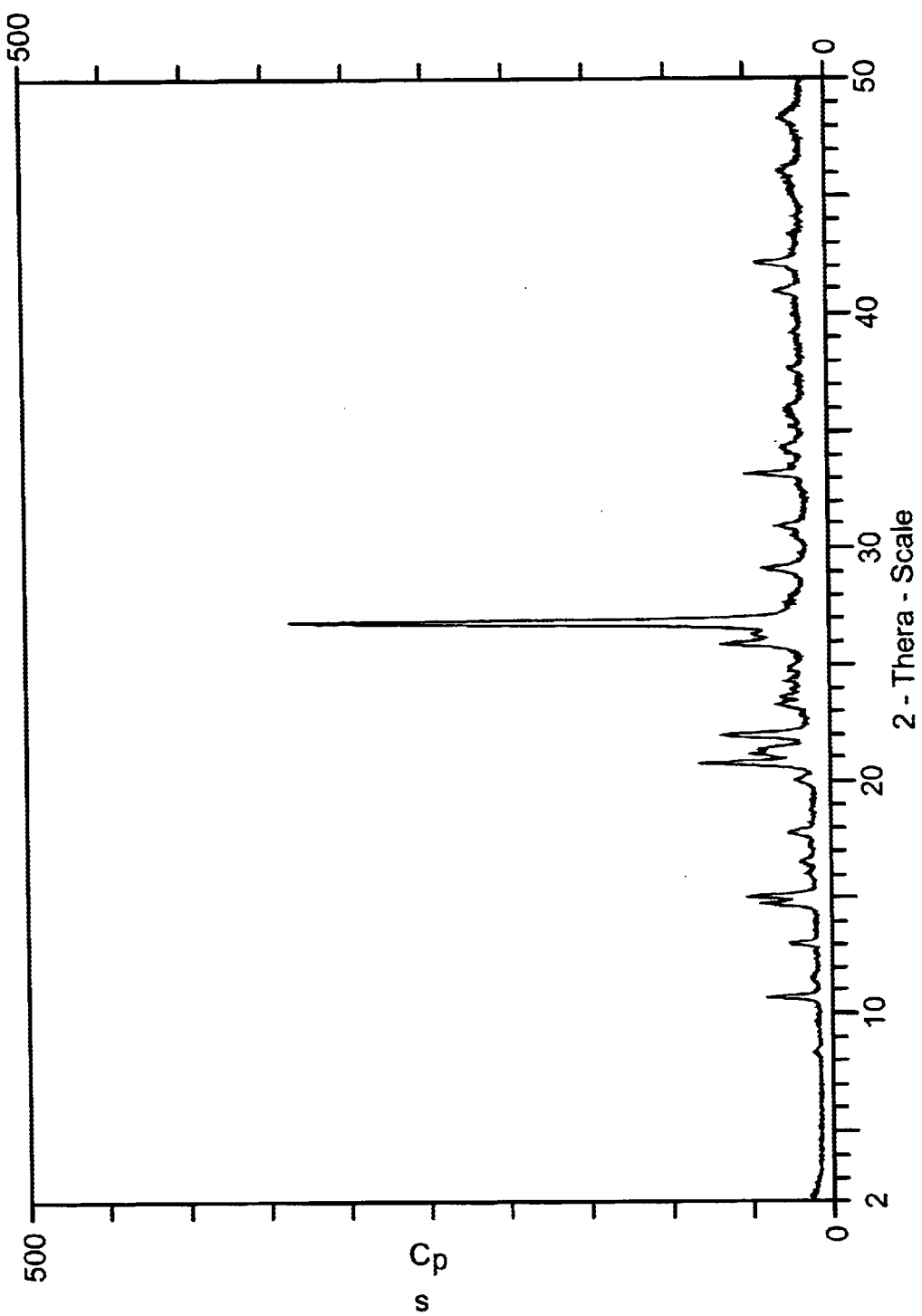
FIG. 2 is a PXRD trace of the monohydrate (IA) prepared in Example 9.

The zwitterion monohydrate (IA) contains one mole equivalent of water, i.e. 5.29% by weight. There two separate weight loss events between 80–140° C. (1.9%) and 140–200° C. (3.2%) when analysed by TGA and also by TG-MS analysis (FIG. 1). Small endothermic events around 132° C. and 183° C. associated with dehydration events, followed by an anhydrous melt at around 296° C. were apparent when analysed by DSC (FIG. 1). A PXRD trace of (IA) is shown in FIG. 2.

Example 10

Formulation Example

| Ingredient | % (w/w) |
| --- | --- |
| zwitterion monohydrate (IA) | 0.0312–1.0361[1] |
| Xanthan gum | 2.00 |
| Lutrol F127 | 0.20 |
| Sodium chloride | 0.70 |
| Sodium acetate trihydrate | 0.24[2] |
| Glacial acetic acid | 0.14[2] |
| Water for injections | ad 100.00 |

[1]0.03–1.00% (w/v)
[2]Acetate buffer pH 5.5 (20 mM)

The above formulation can be autoclaved without any form change or detrimental effect on the formulation pH or viscosity.

Example 11

IB, mono-DMSO-solvate

Figure 3:
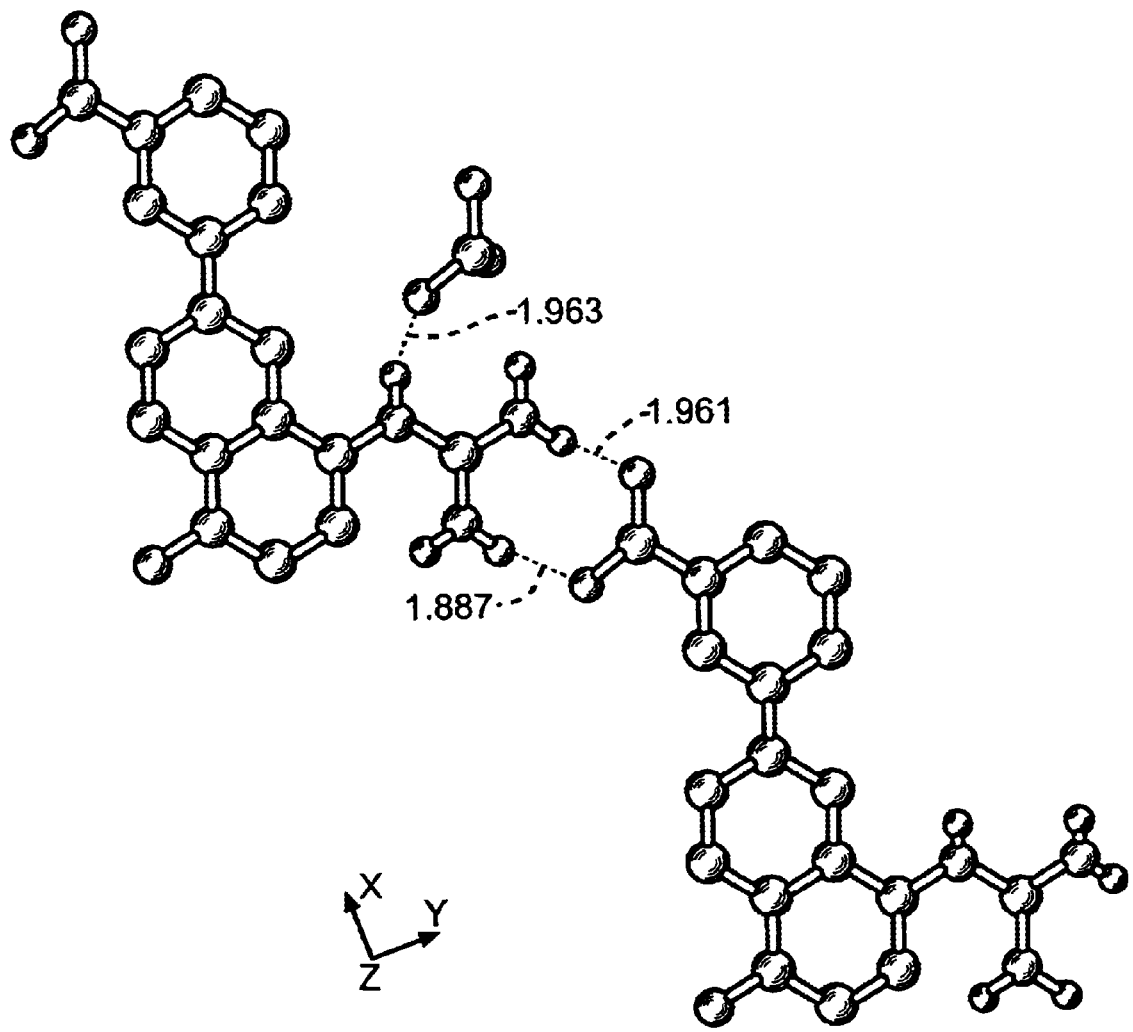
FIG. 3. shows the crystal structure of the compound of (IB), the mono-DMSO-solvate of the compound of formula (IB).
Figure 4:
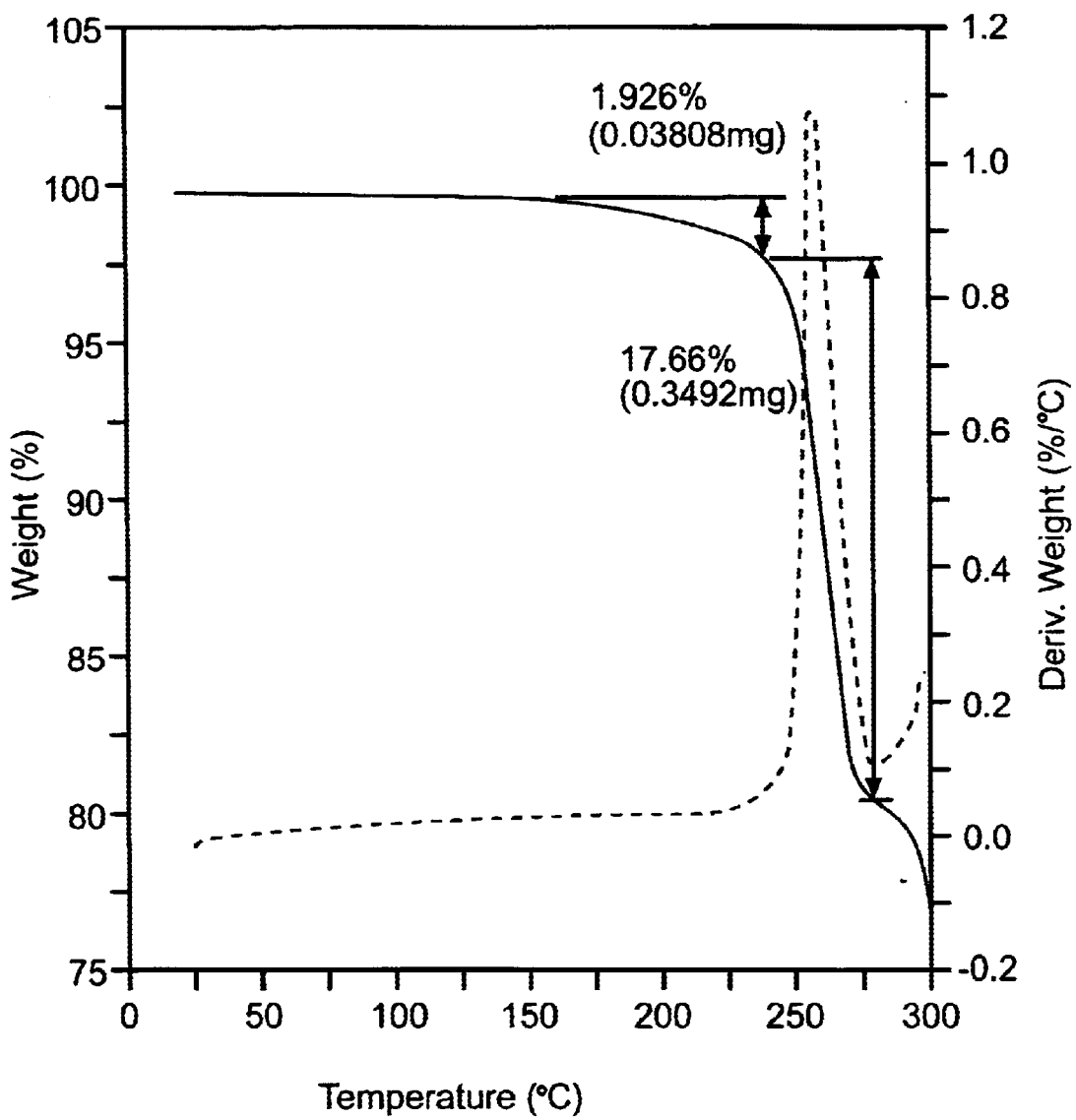
FIG. 4 is a TGA analysis plot of the mono-DMSO-solvate of the compound of formula (IB).
Figure 5:
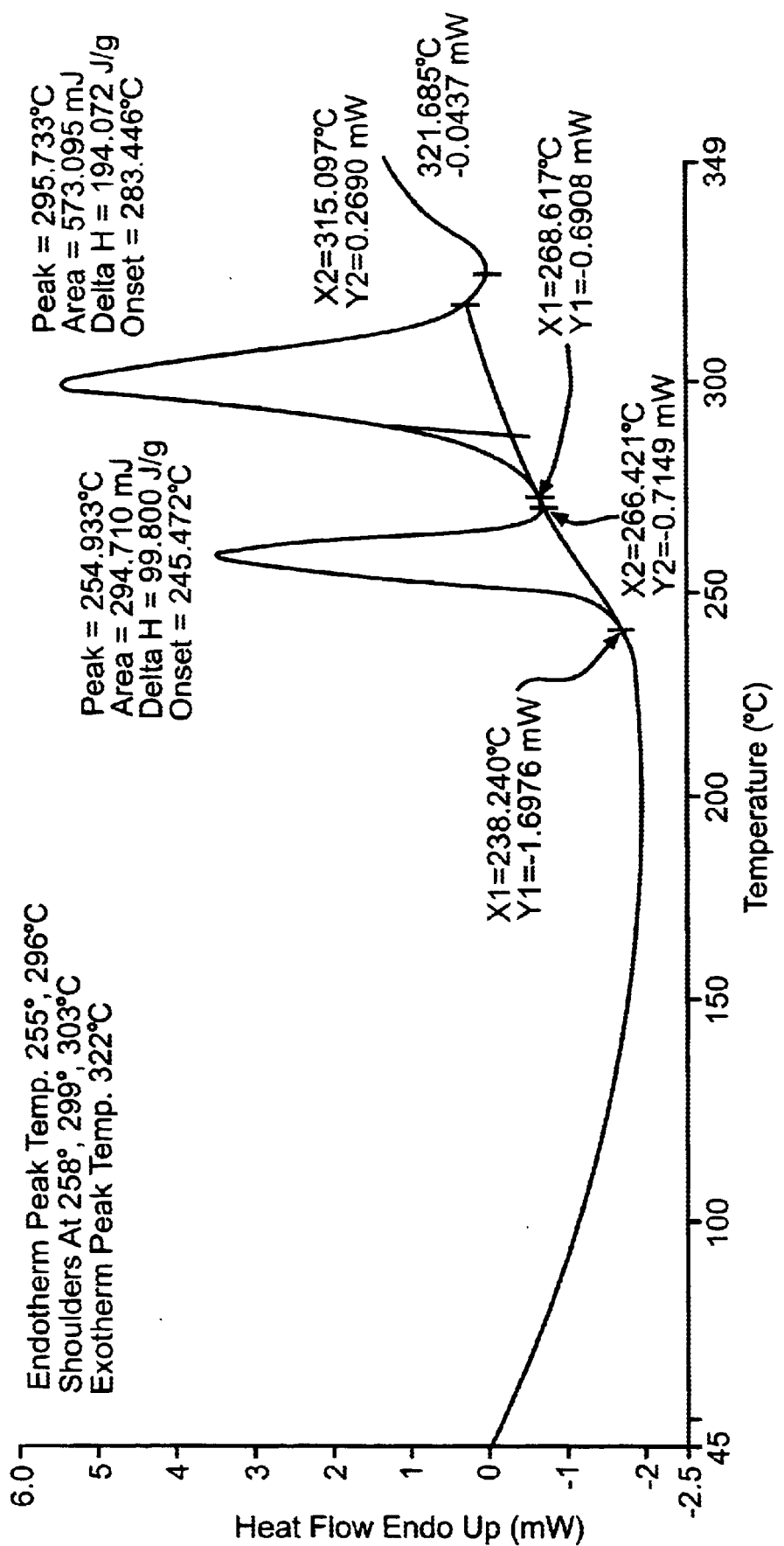
FIG. 5 is a DSC analysis plot of the mono-DMSO-solvate of the compound of formula (IB).

The zwitterion mono-DMSO-solvate (IB, solvent=DMSO) has a crystalline form. The crystal structure, obtained using a single crystal, is shown in FIG. 3. Analysis of the DMSO solvate (IB) by TGA shows a small and gradual weight loss of 1.9% to 250° C. followed by degradation (FIG. 4). Analysis by DSC shows events at 254° C. and 295° C. (FIG. 5).

What is claimed is:

1. A monohydrate of formula (IA)

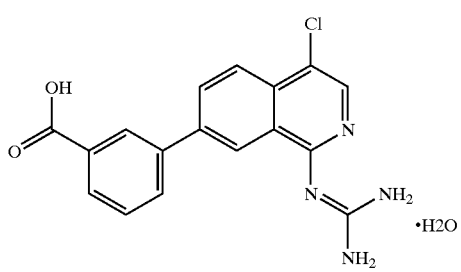
(IA)

or the tautomers or zwitterions thereof.

2. A mono-DMSO-solvate of formula (IB)

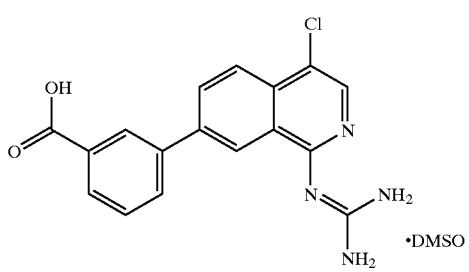
(IB)

or the tautomers or zwitterions thereof.

3. A pharmaceutical composition comprising the monohydrate of the formula (IA), tautomer or zwitterion thereof of claims 1 or 2, and a pharmaceutically acceptable diluent, adjuvant or carrier.

4. A method of treating a uPA-mediated condition comprising administering a therapeutic amount of a compound according to claim 1 or 2.

5. The method of claim 4, wherein the uPA-mediated condition is selected from the group consisting of chronic dermal ulcer, angiogenesis (neo-vascularization), bone restructuring, embryo implantation in the uterus, infiltration of immune cells into inflammatory sites, ovulation, spermatogenesis, tissue remodelling during wound repair and organ differentiation, fibrosis, local invasion of tumours into adjacent areas, metastatic spread of tumour cells from primary to secondary sites, and tissue destruction in arthritis.

6. A pack comprising a therapeutic effective amount of a compound according to claims 1 or 2 optionally including a pharmaceutically-acceptable adjuvant, carrier or diluent and directions instructing the user on the treatment of a uPA-mediated condition.

7. A carboxylate salt of the formula (IX)

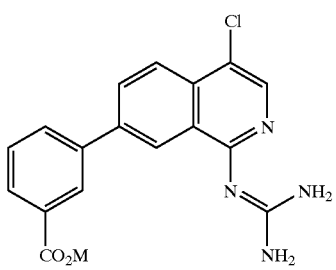
(IX)

or tautomers thereof, and wherein M is Na, K or Li.

8. An acetate, benzoate or p-toluenesulphonate acid salt of the nitrile of formula VIII

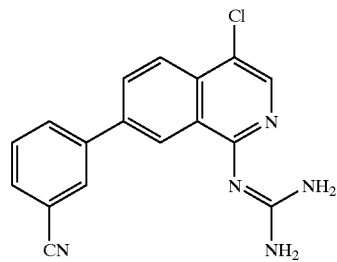
(VIII)

or tautomers thereof.

9. A process for making a compound of claim 1 comprising acidifying the carboxylate salt of the formula (IX)

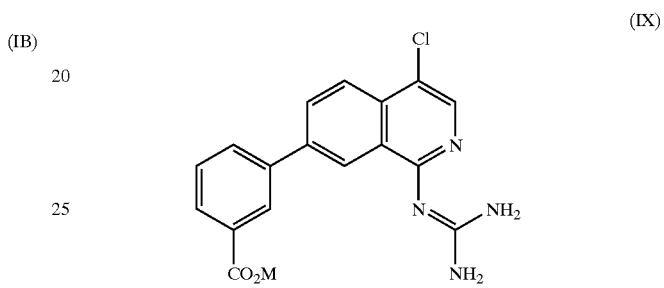
(IX)

or tautomers thereof, and wherein M is Na, K or Li.

10. A process for making a compound of claim 7, which comprises a base-catalysed hydrolysis of an acetate, benzoate or p-toluenesulphonate acid salt of the nitrile of formula VIII

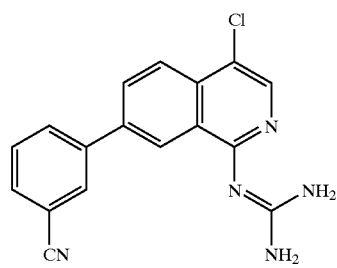
(VIII)

in the presence of a metal cation M+, wherein M is Na, K or Li.

11. A process for making a compound of claim 8 comprising reacting a compound of formula (VI)

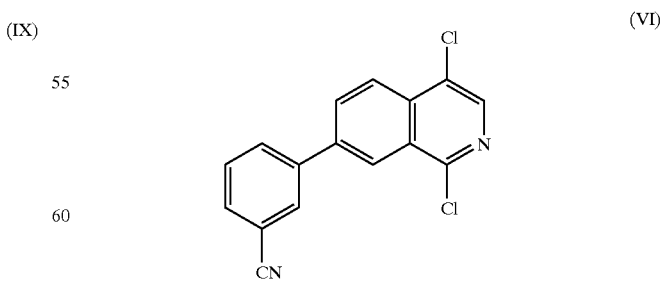
(VI)

with guanidine carbonate or guanidine hydrochloride and potassium t-butoxide.

* * * * *